United States Patent [19]

Gregorio et al.

[11] Patent Number: 4,816,599
[45] Date of Patent: Mar. 28, 1989

[54] BROMOFLUOROETHYLHYPOFLUORITE AND PROCESS FOR ITS PREPARATION

[75] Inventors: Guglielmo Gregorio; Pierangelo Calini, both of Milan; Girogio Guglielmo, Mirano, all of Italy;

[73] Assignee: Ausimont S.p.A., Milan, Italy

[21] Appl. No.: 93,041

[22] Filed: Sep. 4, 1987

[30] Foreign Application Priority Data

Sep. 8, 1986 [IT] Italy ................. 21632 A/86

[51] Int. Cl.$^4$ ........................................... C07C 143/70
[52] U.S. Cl. ................................. 560/300; 260/543 F
[58] Field of Search ..................... 260/543 F; 560/300

[56] References Cited

U.S. PATENT DOCUMENTS 3,769,312  10/1973  Gould et al. ................. 560/300
3,842,156  10/1974  Young ......................... 560/300

OTHER PUBLICATIONS

D. G. Gould, JACS/91:6/Mar. 12, 1969.

Primary Examiner—Paul J. Killos
Attorney, Agent, or Firm—Stevens, Davis, Miller & Mosher

[57] ABSTRACT

The new compound bromofluoroethylhypofluorite, having the formula $CF_2BrCF_2OF$ is obtained by starting from

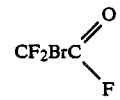

by the reaction in gaseous phase with fluorine, in the presence of a catalyst constituted by CsF on a support constituted by copper (or by another metal) in the form of a porous material having a surface area of at least 0.1 $m^2/g$.

6 Claims, No Drawings

BROMOFLUOROETHYLHYPOFLUORITE AND PROCESS FOR ITS PREPARATION

FIELD OF THE INVENTION

The object of the present invention is the synthesis of a novel compound having the hypofluorite structure, of formula $CF_2BrCF_2OF$. This compound is particularly important as a starting product for the synthesis of bromofluorovinyl-ethers. The bromofluorovinylethers compounds are particularly interesting comonomers in the preparation of fluoroelastomers vulcanizable with peroxides.

BACKGROUND OF THE INVENTION

The preparation of fluoro-oxy-compounds by starting from acyl fluorides by means of the reaction in gaseous phase with fluorine, by a continuous process, is disclosed in the Italian patent application No. 19,847 A/85 in the same Applicant's name.

The preparation process disclosed in the above said patent application is also indicated as suitable for the preparation of bromofluoroalkyl hypofluorites by starting from bromofluorinated acyls. It was observed however that the operating conditions indicated in that patent application, and, in particular, the catalyst based on cesium fluoride therein disclosed and exemplified, are not suitable for obtaining the compound $CF_2Br—CF_2—OF$ in a appreciable amount by a continuous process.

The catalyst according to the above said patent application can be a metal fluoride as such (e.g., Cs fluoride), or it can be prepared by mixing cesium fluoride with a metal material (copper) in the form of chips, or of other compact shapes. In general, the optimum granulometry of CsF is obtained by grinding. The catalyst, when is used for the preparation of the compound according to the above patent application, is deactivated within very short times, of the order of minutes, such as not to allow it to be prepared on an industrial scale.

THE PRESENT INVENTION

We unexpectedly found that bromofluoroethylhypofluorite compound can be synthesized by means of the fluorination of the corresponding bromofluoroacetyl fluoride in an industrial process, if a specific catalyst is used and, furthermore, if the reaction temperature is strictly controlled so to be kept within a very narrow range.

A further object of the present invention is a process for obtaining the compound $CF_2Br—CF_2OF$, accomplished in continuous, and consisting in reacting, in the gaseous phase, bromofluoroacetyl fluoride:

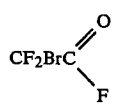

with fluorine, preferably in eccess with respect to the stoichiometric amount, in the presence of a catalyst based on cesium or potassium fluoride, supported on a metal selected from Cu, Fe, Ni, preferably Cu, in the form of a porous material, with a large surface area, higher than 0.1 m²/g and preferably higher than 0.4 m²/g, and with a bulk specific gravity generally lower than 5 g/cm³, preferably, in case of copper, of the order of 3.5–4 g/cm³. The catalyst should have a granulometry suitable for accomplishing a stationary bed, and, in general, it should have a minimum size not lower than 0.05 mm. The fluorination reaction is carried out at a temperature of from 10° to 45° C. and preferably of from 20° to 30° C., and the two reactants are suitably diluted with an inert gas, such as nitrogen or helium, to allow the reaction temperature to be strictly controlled, such a temperature control being made difficult by the exothermic character and the high rate of the same reaction.

The reaction takes place within very short times: for example, at 25° C. the contact time is shorter than 1 minute.

A suitable method for preparing a catalyst having the desired requisites consists in submitting a copper oxide (CuO or Cu₂O, or a mixture of them), in the form of small pieces or granules (small beads, cylinders, etc.) to a reduction with hydrogen diluted with nitrogen, at temperature comprised within the range of from 200° to 500° C., preferably of from 250° to 350° C., a metal copper support being thus obtained, in porous form and with the specific surface area as indicated above. This support is then impregnated with a solution of cesium or potassium fluoride, and the solvent used is evaporated off under vacuum. In general, the amount of CsF or KF which can be fixed on the support is a rather large amount, up to approximately 10% by weight. Even amounts of 3% yield a good catalyst.

The so prepared catalyst shows a high activity, which remains good also after a very long continuous operation: in fact, even after a use of some days, its activity does not show a noticeable decay. Furthermore, should a reactivation become necessary, this can be very simply accomplished inside the same reactor, by means of a hydrogen stream at a temperature of, e.g., 200°–300° C.

In order to strictly control the reaction temperature it is also possible to use said catalyst (cesium or potassium fluoride) in the form of powder, not supported but in suspension in a fluorinated oil such as, for example a perfluoropolyethereal oil (Fomblin YO4 TM).

In this case the fluorinated reaction is carried out at the same conditions described above but the starting compound

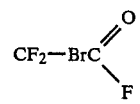

can be injected into the reactor also in a liquid form.

The conversion of

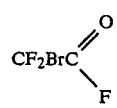

in the process of the present invention is practically total.

The yield of $CF_2BrCF_2OF$ is very high.

The product obtained in the reaction, in the gaseous form, generally diluted with the inert gas and with the possibly used excess of fluorine, can be separated from the gaseous mixture by a low-temperature condensation, at about −80° C., or it can be recovered by dissolution in a fluorocarbon-type solvent, in particular, Delifrene ®.

The following examples are supplied for illustrative purposes, and are not limitative of the possibilities of practical embodiment of the present invention.

EXAMPLE 1

Catalyst Preparation 84 g of Carlo Erba's CuO needles "RS for microanalysis" grade, is charged to a cylindrical glass reactor and is heated under a nitrogen stream (50 Nl/h) up to the temperature of 300° C. A mixture of nitrogen containing 10% of hydrogen is then delivered. The reduction is continued for 3.5 hours. In this way, 67 g is obtained of needles of 0.5 mm of diameter, and having an average length of 5 mm, of spongy metal copper having a surface area of 0.5 m²/g.

The so obtained metal copper is charged to a rotary evaporator and is degassed under vacuum for 30 minutes. A solution of 6 g of CsF dissolved in 10 cc of methanol is then sucked up, and the vacuum-drying is continued for 2 hours.

The so-prepared catalyst is charged to the use reactor, and, before being used, is dried under an inert gas stream at the temperature of 120° C. for two hours.

SYNTHESIS OF CF$_2$Br—CF$_2$OF

A cylindrical reactor of AISI 316, of 30 mm of diameter and 350 mm long, is charged with 610 g of a catalyst CsF on copper prepared as disclosed above. The amount of cesium fluoride deposited on the metal results to be equal to 8% by weight.

The reactor is maintained at the controlled temperature of 25° C., and to it a gaseous mixture of 1 Nl/h of fluorine and 0.5 Nl/h of CF$_2$Br—COF is fed. Furthermore, diluent helium is fed at the flowrate of 30 Nl/h. With these gas flowrates, the contacy time results to be of about 30 seconds.

The reaction mixture leaving the reactor is analysed by I.R. spectrophotometry and gas-chromatography. By GLC, the disappearance is observed of the starting product CF$_2$BrCOF, and the presence is observed, together with the unreacted excess of fluorine supplied, of only one product corresponding to CF$_2$Br—CF$_2$OF.

A similar result is obtained from IR analysis, with the disappearance of the carbonyl band due to the initial product, and the presence of an absorption band at 1,300 cm$^{-1}$, to be attributed to the hypofluorite.

The $^{19}$F-NMR analysis performed at −35° C. has shown signals (δ, ppm from CCl$_3$F) at: −95 attributed to —CF$_2$—Br; −65.5 attributed to —CF$_2$—OF; +139.7 attributed to —OF.

EXAMPLE 2

(Comparative Example)

The cylindrical reactor of AISI 316 of the preceding example is charged with 500 g of catalyst CsF on copper prepared by evaporating a methanol solution of CsF in a rotary evaporator in the presence of copper turning chips and sieving the residue.

The amount of CsF stably deposited on the copper resulted in this preparation equal to 1.5% by weight.

The reaction is carried out by operating as in the preceding example. The reaction mixture leaving the reactor is analysed after 30 minutes by gas-chromatography: a partial conversion (10%) of the initial product, as well as the presence of small amounts (5%) of BrCF$_2$—CF$_2$OF identified as in the preceding example are observed.

After a 2-hour run, the catalytic activity results minimum, and by GLC the presence of the practically unaltered initial product is demonstrated.

EXAMPLE 3

A reactor of AISI 316 having 0.8 liters of capacity is charged with 200 g of commercial CsF in the form of powder in the presence of 500 ml of a fluorinated oil Fomblin Y04 ® of Montedison.

Said reactor is externally cooled by water. To this reactor 2.5 g/h of liquid CF$_2$Br—COF and a gaseous mixture of 3.4 l/h of helium containing 12% vol. of fluorine are fed. The gaseous stream leaving the reactor contains an amount of 2% of unreacted excess of fluorine and some unidentified products having low boiling point in a quantity less than 1% vol. beside the reaction product CF$_2$BrCF$_2$OF.

It is observed that the starting product CF$_2$BrCOF is almost completely reacted (over 95%) and it is converted in CF$_2$BrCF$_2$OF.

Said product is detected by gas-chromatography as already stated in the previous examples.

What we claim is:

1. 2-Bromo-perfluoroethyl-hypofluorite.

2. Process for preparing 2-bromo-perfluoroethyl-hypofluorite consisting in reacting, in the gaseous phase, by a continuous process,

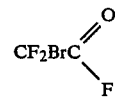

with fluorine, at a temperature comprised within the range of from 10° to 45° C., in the presence, or not, of an inert gaseous diluent, in the presence of a catalyst comprising cesium or potassium fluoride, supported on a metal selected from Cu, Fe, Ni, in the form of a porous material having a specific surface area of at least 0.1 m²/g, and a minimum particle size not lower than 0.05 mm.

3. Process according to claim 2, wherein the catalyst is prepared according to the following steps:
 (a) reduction with H$_2$ diluted with N$_2$, at 200°-500° C., of copper oxide in the form of pieces of small dimensions (granules, small beads, small cylinders);
 (b) impregnation of the so-obtained porous support with CsF solution;
 (c) removal of the solvent under vacuum.

4. Process according to claim 2, wherein the reaction is carried out in the presence of an excess of fluorine relatively to the stoichiometric amount.

5. Process for preparing 2-bromo-perfluoroethyl-hypofluorite consisting in reacting by a continuous process

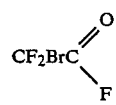

at a temperature comprised within the range of from 10° to 45° C., with fluorine in the presence, or not, of an inert gaseous diluent, in the presence of a catalyst comprising cesium or potassium fluoride, in the form of powder and suspended in an inert fluorinated oil, the reactant

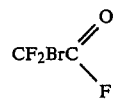
being fed in liquid or vapor state.
6. Process according to claim 5 wherein said inert fluorinated oil is a perfluoroalkylpolyether.
* * * * *